United States Patent [19]

Fortner et al.

[11] 4,198,982
[45] Apr. 22, 1980

[54] SURGICAL STAPLING INSTRUMENT AND METHOD

[75] Inventors: Joseph G. Fortner; Dimitrios Papachristou, both of New York, N.Y.

[73] Assignee: Memorial Hospital for Cancer and Allied Diseases, New York, N.Y.

[21] Appl. No.: 892,363

[22] Filed: Mar. 31, 1978

[51] Int. Cl.$^2$ ............................................. A61B 17/04
[52] U.S. Cl. .................................. 128/334 C; 227/19
[58] Field of Search ............... 128/334 R, 334 C, 305, 128/337; 227/8, 19, 76

[56] References Cited

U.S. PATENT DOCUMENTS

| | | | |
|---|---|---|---|
| 3,388,847 | 6/1968 | Kasulin et al. | 227/19 |
| 3,552,626 | 1/1971 | Astafiev et al. | 128/334 C X |
| 3,593,903 | 7/1971 | Astafiev et al. | 227/19 X |
| 3,790,057 | 2/1974 | Razgulov et al. | 227/19 |

FOREIGN PATENT DOCUMENTS 1057729  3/1954  Fed. Rep. of Germany ....... 128/334 C Primary Examiner—Stephen C. Pellegrino
Attorney, Agent, or Firm—Sprung, Felfe, Horn, Lynch & Kramer

[57] ABSTRACT

A method and a surgical stapling instrument for the stapling together of the free ends of two hollow organs. The instrument comprises an elongated tubular body, a base unit concentrically connected to the body and a head unit mounted to the body and concentric therewith for relative movement with respect to the head unit over a range wherein the inner end thereof is spaced apart from the outer end of the base unit and wherein the inner end of the head unit is substantially adjacent to the outer end of the base unit. Holding elements are mounted on the base and head units and project outwardly from the outer and inner ends thereof respectively to extend between the base and head units and are disposed inwardly from the outer periphery of the ends of the base and head units for holding the free ends of the hollow organs inwardly of actuatable stapling and cutting mechanisms to maintain the free ends in position on the base and head portions while the base and head units are moved towards one another. The method includes inserting the instrument into an incision in one hollow organ with the base and head units substantially adjacent until the head unit is inserted into the free end of the other organ, separating the two units until the base unit is in the free end of the one organ, connecting the free ends to the holding elements, moving the head and base units towards each other until substantially adjacent, actuating the stapling and cutting mechanisms, separating the two units and withdrawing the instrument from the organs.

10 Claims, 11 Drawing Figures

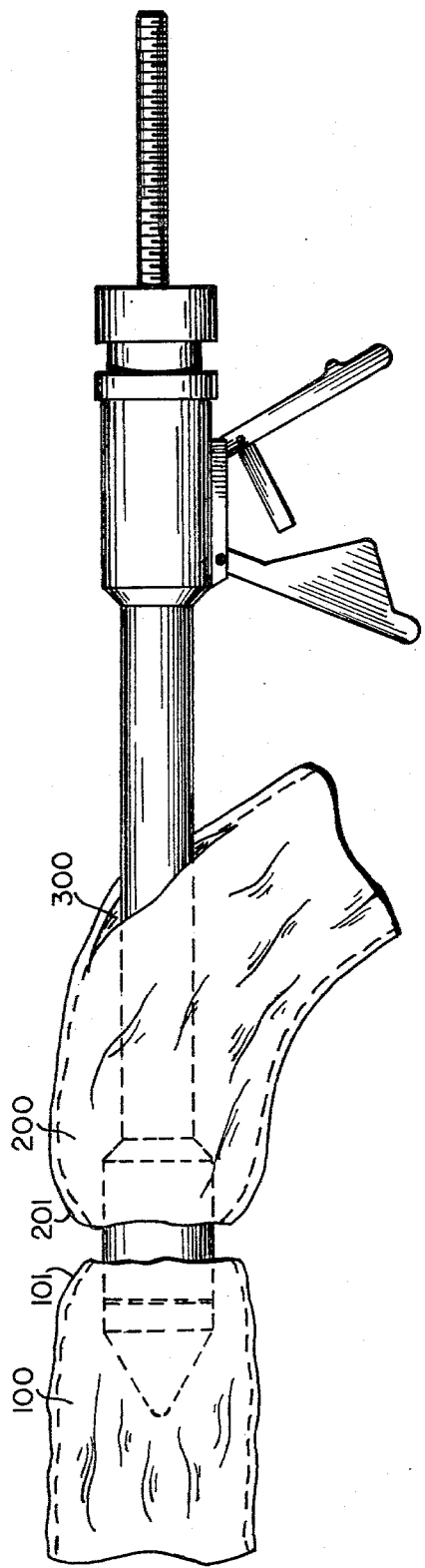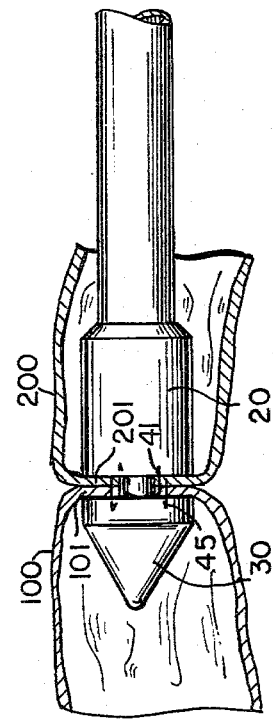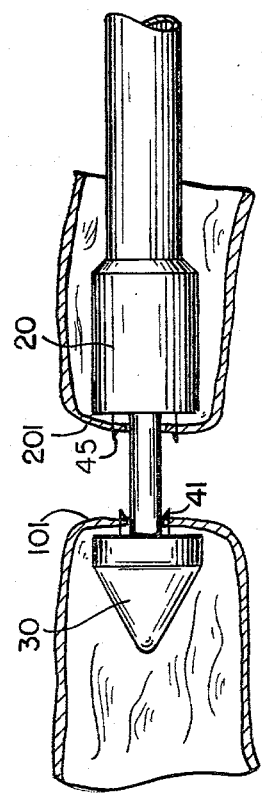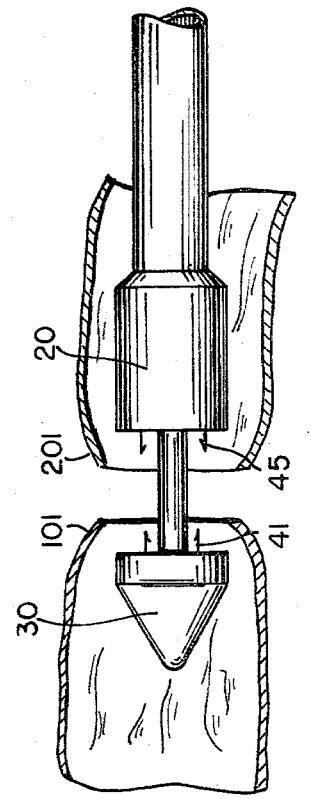

SURGICAL STAPLING INSTRUMENT AND METHOD

BACKGROUND OF THE INVENTION

The present invention relates to a method and surgical stapling instrument for the stapling together of the free ends of two hollow organs.

Surgical staplers are known in the prior art, but these do not have the capability of producing a circular series of staples to effect the joining together of two hollow organs.

Another type of stapling apparatus which can accomplish a series of circular staples is the type wherein the hollow organs are everted and then stapled outwardly of the organ. An example of this type of apparatus is disclosed in U.S. Pat. No. 3,606,888.

Lastly, surgical stapling instruments of the type wherein the hollow organs are first inverted and thereafter stapled within the confines of the connected hollow organs are shown in U.S. Pat. Nos. 3,193,165, 3,388,847, 3,552,626 and 3,593,903.

While it has been found that the inverting type of circular stapler has distinct advantages in the healing process over the everting type of stapler, the known circular stapling instruments have the disadvantage that a purse string suture must first be inserted at the free ends of the hollow organs in order to tie the periphery thereof inside the stapler line. When one is working in the depth of the chest or in the pelvis, to insert such a suture necessitates a considerable amount of time, and the time in which it takes to carry out this suturing negates the purpose of the circular stapler, which is to effect a speedy and reliable connection to the two hollow organs.

While apparatus have been suggested for effecting the eversion of the hollow organs, such as in U.S. Pat. No. 3,908,662, the inverting surgical stapling instruments still have this serious drawback.

SUMMARY OF THE INVENTION

The present invention provides a stapling instrument which eliminates the disadvantages of the prior art surgical stapling instruments.

The present invention also provides holding elements disposed within the radial line of the staples to maintain the free ends of the hollow organs in position on the various portions of the stapling instrument so that the stapling instrument can be used without the need of suturing the free ends of the hollow organs.

The present invention further provides cutting means having a knife blade which is removably mounted in the instrument so that it can be removed and disposed of after each use.

The present invention also provides two radial rows of staples, wherein the inner and outer rows alternate to prevent leaks and any postoperative hemorrhaging.

The method of stapling eliminates the disadvantages of the prior art methods. These are achieved by the surgical stapling instrument of the present invention comprising an elongated tubular body, a base unit concentrically connected to the body and a head unit concentrically mounted to the body. The base unit has a substantially cylindrical outer end and is positionable in one hollow organ to dispose the outer end portion thereof adjacent to the free end of the hollow organ. The head unit has a substantially cylindrical inner end and means mount the head with the inner end thereof face-to-face with the outer end of the body unit for relative movement with respect to the body unit over a range wherein the inner end of the head unit is spaced apart from the outer end of the base unit and wherein the inner end of the head unit is substantially adjacent to the outer end of the base unit. The head unit is positionable in the other hollow organ to dispose the inner end thereof adjacent to the free end of the other hollow organ.

Actuatable stapling means comprises a first portion thereof disposed in the base unit and a second portion thereof aligned with the first stapling portion and disposed in the head unit. The first and second stapling portions are concentric with the tubular body and disposed in the annular area inward of the outer periphery of the outer and inner ends of the base and head units respectively. The stapling means staple the two free ends together, upon actuation, when the base and head units are substantially adjacent.

Holding means are mounted on the base and head units and project outwardly from the outer and inner ends thereof respectively to extend therebetween and are disposed in the annular area inwardly of the annular area of the first and second stapling portions for releasably holding the free ends of the hollow organs inwardly of the stapling portions to maintain same in position on the base and head units during the relative movement of the base and head units towards each other and during the actuation of the stapling means.

Actuatable cutting means comprises a first portion thereof disposed in the base unit and a second portion aligned with the first portion and disposed in the head unit. The first and second cutting portions are disposed concentric with the tubular body and positioned in the annular area between the holding means and the stapling means. The cutting means cuts off excess tissue inwardly of the staples, upon actuation, when the base and head units are substantially adjacent.

Manual means are provided to actuate the stapling means and the cutting means.

In a preferred embodiment, the holding means comprises a plurality of barbed spear-like projecting elements on the base and head units. Additionally, the projecting elements may be radially aligned so as to be interdigitated and they overlap longitudinally when the base and head units are substantially adjacent to effect the reception of each element through both free ends thereby obtaining a holding of each of the hollow organs by all of the projecting elements.

In another preferred embodiment, the base and head units each have mounting bores therein and the holding means further comprises a plurality of mounting members each for holding one projecting element at one end and each received at the other end in one mounting bore. The mounting members can be releasably retained in the mounting bore so that the elements can be removed when desired.

Another preferred embodiment of the present invention utilizes two concentric rows of staples so that the first stapling portion comprises two concentric rows of staple chambers and two concentric rows of staple anvils which are aligned with the staple chambers. Each row of staple chambers and anvils are evenly distributed with the outer row of anvils overlapping each two adjacent anvils in the inner row and consequently the same configuration in the staple chambers.

The cutting means, in a preferred embodiment, comprises a cylindrical knife blade in the base unit and an annular resilient cutting pad in the head unit. The knife coacts with the pad to cut when the knife is moved into the pad by the actuating means. The knife blade is preferably removably mounted in the base so that it can be removed and disposed of after each use.

The method includes inserting the instrument into an incision in one hollow organ with the base and head units substantially adjacent until the head unit is inserted into the free end of the other hollow organ, separating the two units until the base unit is in the free end of the one organ, connecting the free ends to the holding means, moving the base and head units towards each other until substantially adjacent, actuating the stapling and cutting means, separating the two units and withdrawing the instrument from the organs.

BRIEF DESCRIPTION OF THE DRAWINGS

The invention will be further understood and its advantages more fully appreciated from the following detailed description of the preferred embodiments thereof when taken into conjunction with the accompanying drawings, wherein:

FIG. 5 shows the insertion of the instrument into two hollow organs;

FIG. 6 is a detailed view of units separated in the organs;

FIG. 7 is a detailed view of the holding of the free ends of the organis with the units separated;

FIG. 8 is a detailed view of the instrument during use with the units substantially adjacent;

DETAILED DESCRIPTION OF THE INVENTION

Figure 1:
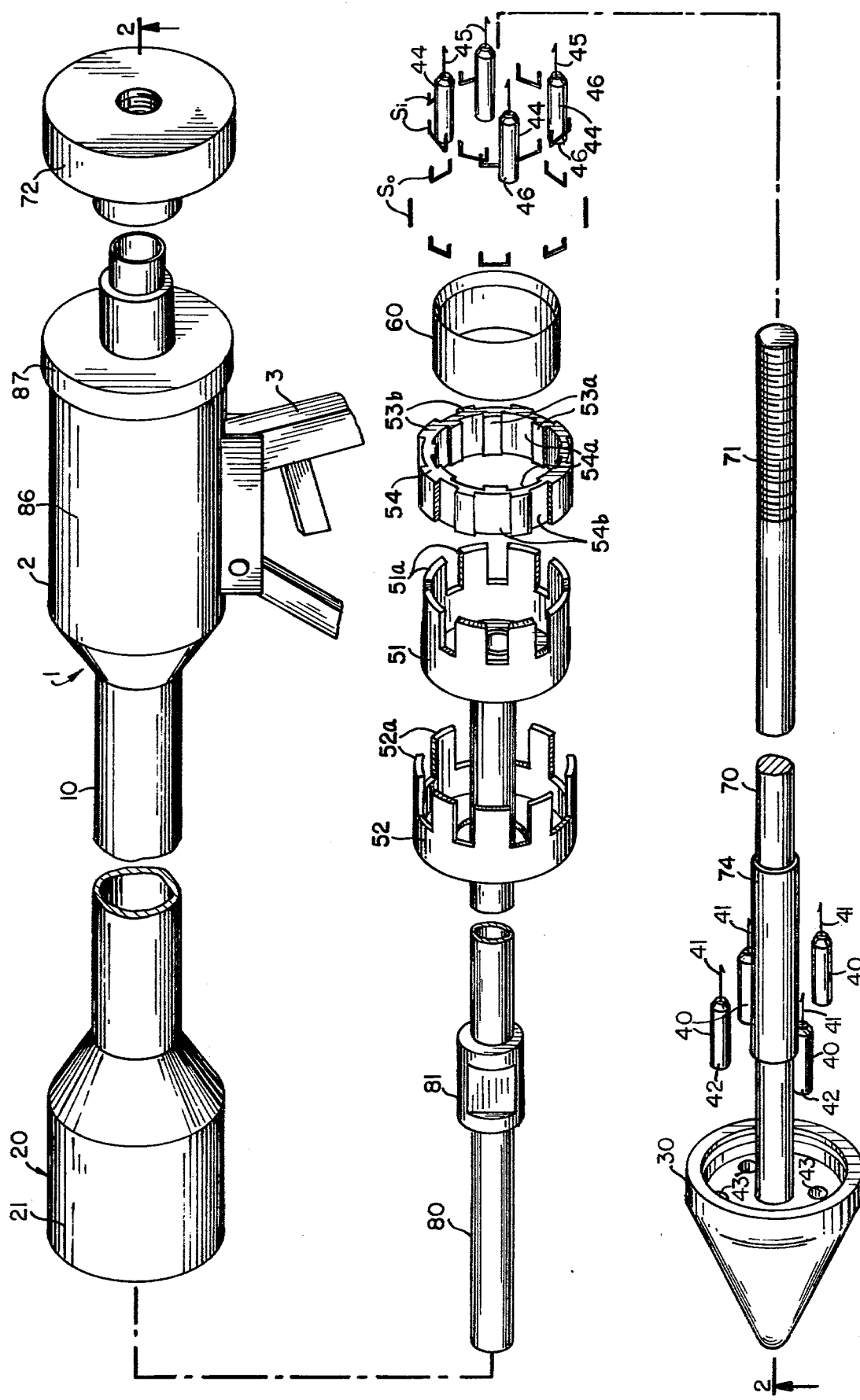
FIG. 1 is an exploded perspective view of the surgical instrument in accordance with the invention.

Referring to FIG. 1, the stapling instrument 1 includes a barrel 2 having a handle 3 connected thereto, an elongated tubular body 10, a base unit 20 concentrically connected to the body 10 and a head unit 30 concentrically connected with respect to the base 20.

Figure 2:
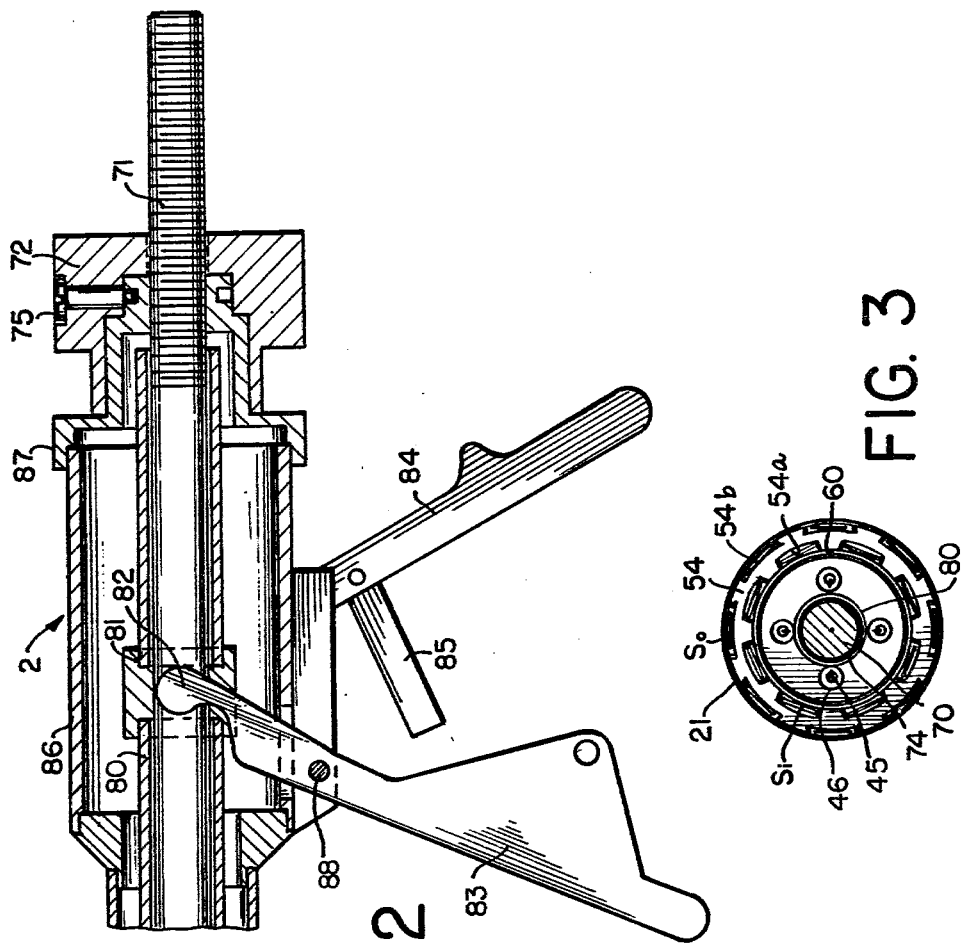
FIG. 2 is a sectional view of the surgical instrument that's taken along line 22 of FIG. 1.

Referring now to FIGS. 1 and 2, base 20 is connected to tubular body 10 by set screws 22 so as to be stationary with respect thereto. Extending through tubular body 10 is hollow rod 80 having a driving joint 81 thereon which is engageable with the elements of handle 3. Fixedly mounted in rod 80 is a hollow rod 74 which slideably receives rod 70 therein having threaded portions 71 and 73 at either ends thereof.

Handle 3 includes a stationary member 84 and a pivotable member 83 which pivots about pivot axis 88 and which has a cam member 82 at one end thereof which coacts with driving joint 81 to move rod 80 longitudinally through tubular body 10. Safety catch 85 is pivotable at one end to move out of the way of handle element 83 so that it can be moved towards handle element 84 to effect the movement of rod 80.

Threaded end 73 of rod 70 is threadably engaged into head 30 which has a tapered end 32 for facilitating the entry of the instrument into an organ and which has a substantially cylindrical inner end portion 31 which is concentric around rod 70. The other threaded end 71 of rod 70 projects from the rear of barrel 2 which includes a cylindrical portion 86 and a cap 87 fixedly mounted thereon. Threadably engaged with threaded portion 71 is an adjusting nut 72 which has a set screw 75 therein which is tightenable to fix the adjusting nut in a desired position. Upon the clockwise turning of adjusting nut 72, rod 70 is drawn rearwardly so as to bring head 30 from a space apart position with respect to base 20 to a position where they are substantially adjacent to one another. By turning the adjusting nut in the counterclockwise direction, head 30 and base 21 are moved apart from each other. Base 20 has a substantially cylindrical end portion 21 which is concentric with rod 70 and therefore concentric with end portion 31 of head 30.

Figure 3:
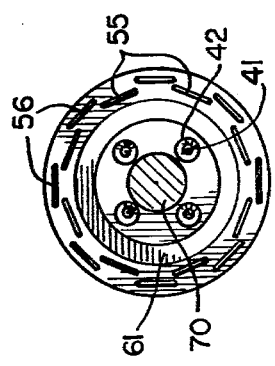
FIG. 3 is a sectional view taken along line 3—3 of FIG. 2.
Figure 11:
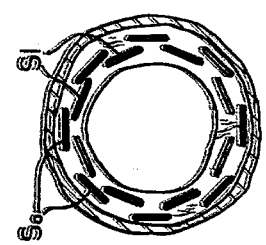
FIG. 11 is a sectional view along line 11—11 of FIG. 10.

The actuable stapling means of the instrument is described with reference to FIGS. 1-4. The stapling means includes a portion in the base 20 and in the head 30. Situated in base 20 are staple pushing elements 51 and 52, element 51 having a plurality of inner pushing members 51a and element 52 having a plurality of outer pushing members 52a each disposed in a circle. Staple pushing elements 51 and 52 are fixedly connected to rod 80 and movable therewith and therefore movable with respect to base 20. Disposed between the staple pushing elements 51, 52 is cylindrical sleeve 54 which is fixedly connected to base 20 and which has inner and outer teeth 53a and 53b and slots 54a and 54b defining staple holding chambers with cylindrical end 21 and knife 60 and in which staples 51 and Si and So are received in front of the staple pushing members 51a and 52a respectively. As shown in FIG. 3, the slots 54a and 54b and consequently the staple pushing elements 51a and 52a respectively which are aligned with the slots, are situated in two concentric circular patterns wherein the outer row overlaps the inner row so that no free space is left therebetween. In the embodiment shown, there are eight staples in the inner row and eight staples in the outer row and consequently eight staple chambers in each row and eight staple pushing elements in each row. The staples Si and So are received in slots 54a and 54b respectively and rest on the ends of staple pushing elements 51a and 52a respectively when the instrument is in the position shown in FIG. 2.

Situated in the head 30, are staple anvils 55 and 56 which are also situated in two concentric circles and which are aligned with slots 54a and 54b respectively. The configuration of these anvils is clearly illustrated in FIG. 4. When the staples are pushed from the staple slots into the anvils, the anvils coact therewith to effect the closing of the staples.

In operation, when the head 30 is brought adjacent to base 20, the anvils 55 and 56 are aligned with slots 54a and 54b respectively. Upon the closing of the handle elements 83 and 84, the stapling means is actuated whereupon, rod 80 is pushed forward thereby moving staple pushing elements 51, 52 forward with respect to the cylindrical sleeve 54. As a result, staples Si and So are pushed forward into anvil 55 and 56 and the staples are closed.

The actuable cutting means of the instrument includes a portion on base 20 and a portion on head 30. Situated in base 20 is the cylindrical knife blade 60 which is disposed in the annular region concentrically around the body 10 and inwardly of the stapling means. The knife is disposed in such a position such that the end of blade 60 is disposed substantially flush with the end of the cylindrical portion 21 of the base. The blade 60 is removably mountable in the base and can be retained therein by either a friction fit, a set screw of any equivalent mounting means. The knife blade is connected in the base so as to be stationary with respect to rod 80 and therefore movable with respect to base 20. Disposed in head 30 is an annular pad 61 which is radially aligned with blade 60 and coacts therewith to effect cutting of tissue disposed therebetween. The pad 61 is preferably composed of a hard rubber or plastic so as to enable coaction with the blade 60 without damaging the blade. The cutting means is actuated by the movement of handle members 83 and 84 towards each other during the stapling operation. Upon moving the handle elements together, when head 30 is adjacent to base 20, rod 80 is moved forward thereby moving blade 60 forward and into contact with pad 61.

In order to facilitate the use of the stapling instrument when inserted into two hollow organs as shown in FIG. 6, holding means are provided including holding elements 40 disposed on head 30 and holding elements 44 disposed on base 20. Holding elements 40 comprise cylindrical mounting members 42 which are received at one end in bores 43 disposed in head 30 and having barbed spear-like elements 41 projecting outwardly therefrom. Base 20 also has corresponding elements 44 comprising cylindrical mounting members 46 disposed at one end in mounting bores 47 and having barbed spear-like projecting elements 45 extending outwardly from the end 21 of the base.

Figure 4:
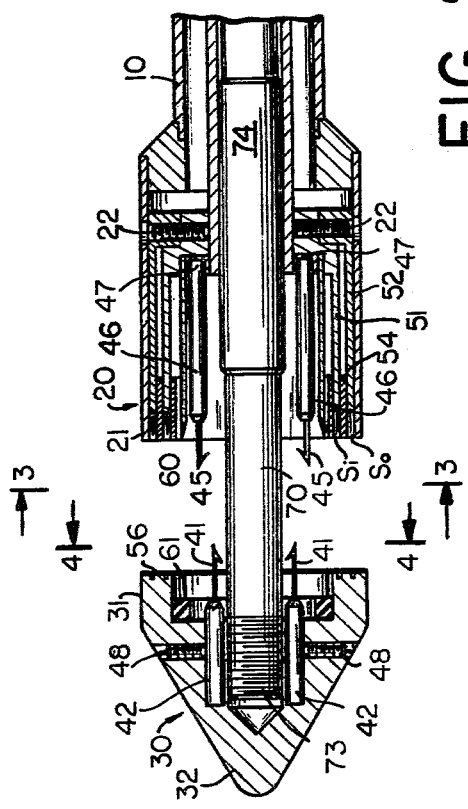
FIG. 4 is a sectional view taken along line 44 of FIG. 2.
Figure 9:
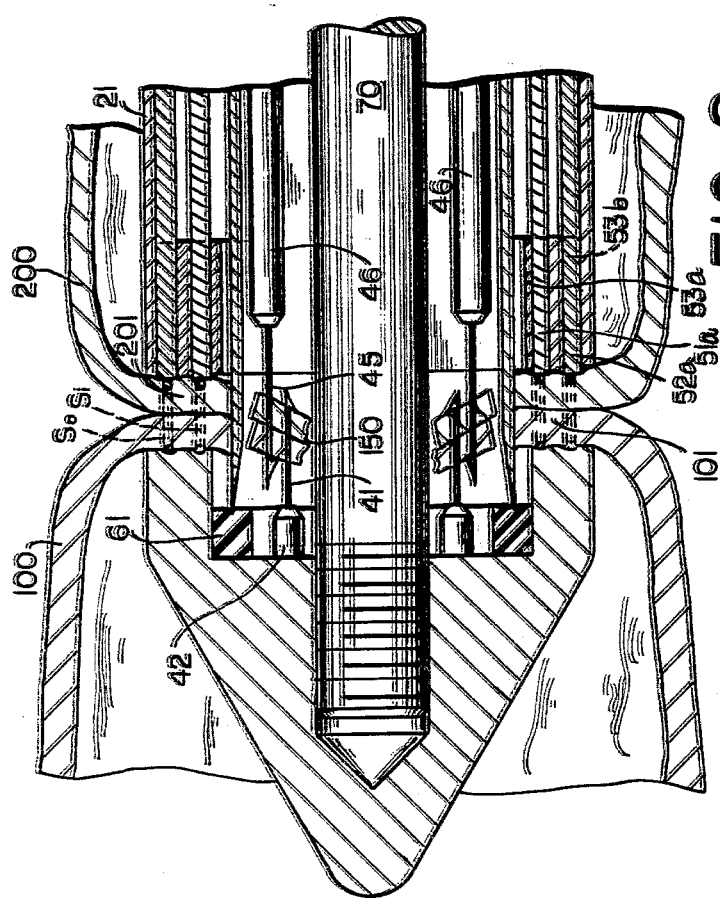
FIG. 9 is a sectional view of the instrument during stapling and cutting.
Figure 10:
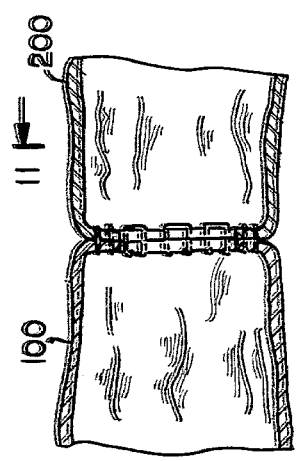
FIG. 10 is a sectional view of the two hollow organs after removal of the instrument.

The projecting elements 41, 45 project inwardly with respect to head 30 and base 20 and extend outwardly from the edges of the head and base so that they overlap when the head 30 and base 20 are substantially adjacent to one another as shown in FIGS. 8 and 9. Additionally, the holding elements 40 and 44 are radially aligned in an annular region inwardly of the annular regions of both the stapling means and the cutting means and are interdigitated as shown in FIGS. 3 and 4 so that they do not conflict when the head 30 and base 20 are brought adjacent to one another.

The mounting of the mounting members 42, 46 is such that they are releasably held in bores 43, 47 respectively. As shown in the embodiment of FIG. 2, set screw 48 is used to hold the mounting member 42 in place.

In the embodiments shown, four holding elements are disposed on the base and four holding elements are disposed on the head, however, these numbers can be varied to produce substantially the same results in operation.

The operation of the surgical stapling instrument will be discussed with reference to FIGS. 5-11 which show the various stages of use of the instrument.

With the head 30 and the base 20 substantially adjacent to one another, the stapler is inserted into an incision 300 in a hollow organ such as a bowel. The head 30 is permitted to remain in the distal bowel lumen 100 having free end 101 while the base 20 is gradually withdrawn (as shown in FIG. 6), by the counterclockwise turning of adjusting nuts 72, into the proximal bowel 200 having free end 201. As shown in FIG. 7, end 101 of the distal bowel is grasped with a forceps and is hooked onto the holding elements 40 on the head and end 201 of the proximal bowel 200 is grasped with the forceps and is hooked on the holding elements 44 on the base. In this way, the free ends of the distal and proximal bowels are held inwardly of the stapling and cutting means. The head is then approximated to the base 20 as a result of the clockwise rotation of adjusting nut 72, so that the head 30 and base 20 are approximately adjacent to each other as shown in FIG. 8 and the projecting elements 41, 45 overlap.

As is clearly shown in FIG. 9, when the base and head are substantially adjacent to one another, the spear-like projecting elements 41, 45 overlap and thereby pierce the other free-end of the bowel being held by the other holding elements. In this way, the bowel is kept under tension during the stapling and cutting operation because actually there are 8 holding elements, instead of 4 holding elements, keeping it in place.

Upon the releasing of the safety release 85, the two handle elements 83 and 84 are manually squeezed together thereby effecting the pushing of the staple pushing elements 51, 52 and the movement of the knife 60 into the pad 61. As a result of the same motion of handle, the two circular rows of staples are inserted into the free ends of the proximal and distal bowels thus stapling the two together and the excess tissue 150 disposed inwardly of the staples is cut by the blade 60 and remains connected to the holding elements 41, 45. The head is then separated from the base to release the tissue therebetween and the instrument is then withdrawn from the bowel and the anastomosis is completed. The stapled together organs are shown in side view in FIG. 10 and in cross-section in FIG. 11, where it is clear that the two rows of staples are placed in such an order so that the vessels between the consecutive staples are being clipped and minute anastomotic leaks and immediate post-operative hemorrhage from the anastomotic line are substantially prevented.

While the present embodiments have been illustrated, the invention is in no way limited thereto. The holding means may comprise some other type of projecting elements or elements that are attached to the stapler and hold the free ends of the organs within the cutting means and the stapling means.

What is claimed is:

1. A surgical stapling instrument for the stapling together of the free ends of two hollow organs comprising:
   a. an elongated tubular body;
   b. a base unit concentrically connected to the body, said base unit having a substantially cylindrical outer end portion which is positionable in one hollow organ to dispose the outer end portion thereof adjacent to the free end of the one hollow organ;
   c. a head unit having a substantially cylindrical inner end portion and means mounting the head unit concentric to the body unit with the inner end thereof face-to-face with the outer end of the body unit and for relative movement with respect to the body unit over a range wherein the inner end thereof is spaced apart from the outer end of the base unit and wherein the inner end of the head unit is substantially adjacent to the outer end of the base unit, the head unit positionable in the other hollow organ when the base unit is positioned in the one hollow organ, to dispose the inner end portion thereof adjacent to the free end of the other hollow organ;

d. actuatable stapling means comprising a first portion thereof disposed in the base unit, a second portion thereof aligned with the first portion and disposed in the head unit, the first and second stapling portions disposed concentric with the tubular body and in the annular area inward of the outer periphery of the outer and inner ends of the base and head units respectively, for stapling together the free ends of the hollow organs, upon actuation, when the base and head units are substantially adjacent;

e. means mounted on the base and head units and projecting outwardly from the outer and inner ends thereof, respectively, to extend therebetween an disposed in the annular area inwardly of the annular area of the first and second stapling portions for holding the free ends of the hollow organs inwardly of the stapling portions to maintain same in position on the base and head units during the relative movement of the base and head units toward each other and during the actuation of the stapling means;

f. actuatable cutting means having a first portion thereof disposed in the base unit and a second portion aligned with the first portion and disposed in the head unit, the first and second cutting portions disposed concentric with the tubular body and in the annular area between the holding means and the stapling means for cutting off excess tissue inwardly of the staples, upon actuation, when the base and head units are substantially adjacent; and g. manual means for actuating the stapling means and the cutting means.

2. The instrument according to claim 1, wherein the holding means comprise a plurality of barbed spear-like projecting elements on the base and head units.

3. The instrument according to claim 2, wherein the projecting elements on the base and head units are radially aligned so as to be interdigited and overlap longitudinally when the base and head units are substantially adjacent to effect the reception of each element through both free ends.

4. The instrument according to claim 2, wherein the base and head units each have mounting bores therein and the holding means further comprises a plurality of mounting members each for holding one projecting element at one end and each having the other end mountable in one mounting bore.

5. The instrument according to claim 4, wherein the holding means further comprises means for releasably retaining each mounting member in its mounting bore.

6. The instrument according to claim 1, wherein the second stapling portion comprises two concentric rows of staple anvils, the inner row comprising a plurality of evenly distributed anvils and the outer row comprising a plurality of evenly distributed anvils each overlapping two adjacent anvils in the inner row and the first stapling portion comprises two concentric rows of staple chambers, each row having a plurality of chambers and each chamber receptive of one staple and wherein the chambers and anvils are aligned with each other to effect the closing of the staple in response to the staple being foced against its associated anvil and wherein the manual means includes means for pushing the staples from the chambers and into the anvil when the base and head units are substantially adjacent.

7. The instrument according to claim 1, wherein the first cutting portion comprises a cylindrical knife blade and wherein the second cutting portion comprises an annular resilient cutting pad and wherein the manual means comprises means for moving the knife from a first position wherein the blade edge is at the outer end of base unit to a second position wherein the knife edge is against the pad when the base and head portions are substantially adjacent.

8. The instrument according to claim 7, wherein the knife blade is removably mounted in the base unit.

9. In a method for surgically stapling together the free ends of two hollow organs, of the type wherein a surgical stapling instrument is provided having an elongated tubular body, a base unit connected to the body and a head unit mounted for relative movement with respect to the base unit over a range wherein the base and head units are spaced apart and wherein the base and head units are substantially adjacent, wherein the base and head units have actuatable stapling means disposed in an annular area concentric with the tubular body and inward of the periphery of the base and head units and actuatable cutting means disposed in the annular area concentric with the tubular body and inward of the stapling means, the improvement comprising:

a. inserting the instrument through an incision in one hollow organ with the head and base units substantially adjacent until the head unit is inserted into the free end of the other organ;

b. withdrawing the base unit into the free end of the one hollow organ by moving the head and base units apart;

c. connecting the free end of the one hollow organ to the head and the free end of the other hollow organ to the base at points inwardly of the cutting means by positioning the free ends onto elements projecting outwardly from the head and base units and extending therebetween and disposed inwardly of the cutting means;

d. moving the head and base units substantially adjacent to each other;

e. actuating the stapling and cutting means;

f. separating the base and head units; and g. withdrawing the instrument from the hollow organ.

10. In a surgical stapling instrument for the circular inverted stapling of the free ends of two hollow organs and of the type having relatively movable base and head units having annular actuatable stapling means and annular actuatable cutting means disposed concentric therewith and inwardly thereof, wherein the improvement comprises:

means mounted on the base and head units and disposed inwardly of the cutting means for holding the free ends of the hollow organs inwardly of the stapling means and the cutting means to maintain same in position on the base and head units during movement thereof toward each other and during the actuation of the stapling and cutting means, a. wherein the holding means comprises a plurality of holding elements projecting outwardly from the inner and outer ends of the head and base units respectively and extending therebetween; and b. wherein the holding elements are disposed in an annular area concentric with the stapling means and positioned inwardly of the cutting means.

* * * * *